United States Patent [19]

Cotrel

[11] Patent Number: 5,005,562
[45] Date of Patent: Apr. 9, 1991

[54] IMPLANT FOR SPINAL OSTEOSYNTHESIS DEVICE, IN PARTICULAR IN TRAUMATOLOGY

[75] Inventor: Yves Cotrel, Paris, France

[73] Assignee: Societe de Fabrication de Material Orthopedique, Berck Sur Mer, France

[21] Appl. No.: 369,701

[22] Filed: Jun. 21, 1989

[30] Foreign Application Priority Data

Jun. 24, 1988 [FR] France .................. 88 08538

[51] Int. Cl.$^5$ .............................................. A61F 5/00
[52] U.S. Cl. ...................................... 128/69; 606/59; 606/61
[58] Field of Search ............... 128/69, 70; 411/168; 606/54, 55, 56, 57, 58, 59, 61

[56] References Cited

U.S. PATENT DOCUMENTS 2,992,669  7/1961  Fesmire .................. 411/168
4,411,259 10/1983  Drummond .............. 128/69

FOREIGN PATENT DOCUMENTS 128058 12/1984 European Pat. Off. .
812248  4/1959 United Kingdom .

Primary Examiner—Edgar S. Burr
Assistant Examiner—Moshe I. Cohen
Attorney, Agent, or Firm—Wenderoth, Lind & Ponack

[57] ABSTRACT

This implant comprises a portion (1) intended for anchorage to bone and a body (2) for attachment to a rod (3); the body has a channel defining two side branches (4) and open on both sides of the body in order to be able to receive the rod (3); this implant contains a threaded plug (8), contrived so that it can be screwed into a female thread formed in the inner walls of the two branches (4) so that its two diametrically opposed edges bear on the rod (3), and the face of the plug (8) directed towards the rod (3) is equipped with means of gripping and attaching the plug to the latter, which can thus be clamped in translation and rotation. This arrangement considerably decreases the external bulkiness of the implant, and reduces the number of parts necessary, as well as the corresponding instrumentation.

11 Claims, 4 Drawing Sheets

IMPLANT FOR SPINAL OSTEOSYNTHESIS DEVICE, IN PARTICULAR IN TRAUMATOLOGY

The present invention relates to an implant for an osteosynthesis device, in particular of the spine, of the type comprising a portion intended for anchorage to bone and a body for attachment to a rod in which there is formed a channel opening into a rear portion of the said body, defining two side branches and open on both sides of the body in order to be able to receive the rod.

The portion for anchorage to bone may be, for example, a suitably formed screw or blade.

The bodies of the known implants are either closed, open at the rear or open at the sides.

These implants have the following disadvantages:

the number of elements necessary for the instrumentation is very high, because of the existence of three different types of bodies;

the bodies open at the rear necessitate the use of intra-channel clamping devices, as described for example in French Patent 2,545,350 (83/07,450), constituting additional instrumentation elements which have to be positioned beforehand on the rod;

it is relatively difficult to introduce the rod into the closed-body implants;

the open-body implants must be oriented in a precise manner, and this constitutes an awkward constraint for the practitioner in the case of the use of screws;

the multiplicity and complexity of the elements employed necessitate the use of considerable ancillary equipment;

awkward bulkiness;

the manufacture of the elements of these implants is difficult and costly, and their ablation is also difficult, in particular because of the need to perform cuts.

The aim of the invention is to provide an implant free of these disadvantages.

According to the invention, the implant comprises a threaded plug, contrived so that it can be screwed into a female thread formed in the inner walls of the two side branches constituting the rear end of the body, closing the channel on this side, and so that its two diametrically opposed edges bear on the rod, and the face of the plug directed towards the rod is equipped with means of gripping and attaching the plug to the latter, which can thus be clamped in translation and rotation.

Screwing the plug inside the branches of the body by virtue of the threads provided on the inner walls of the branches ensures that the implant has a minimum bulk.

According to one possible embodiment, the means of gripping comprise a central point made integrally with the remainder of the plug.

These means of gripping may comprise, as a variant, a peripheral ring projecting from the face of the plug, or, preferably, a combination of this peripheral ring and the central point.

Other features and advantages of the invention will emerge in the course of the following description, made with reference to the attached drawings which illustrate one embodiment thereof by way of non-limiting example.

Figure 1:
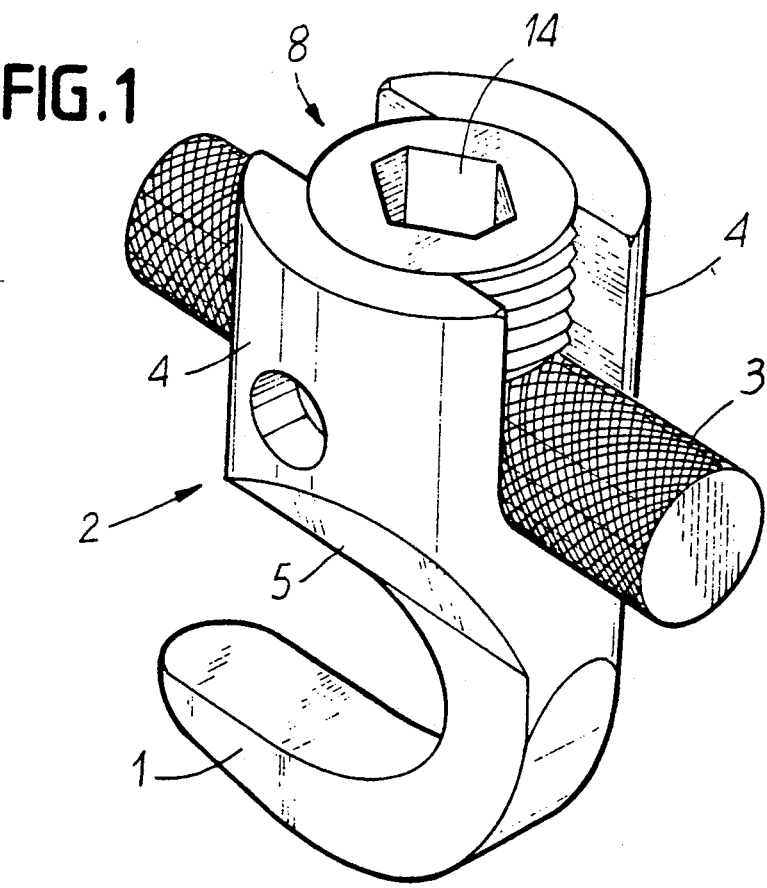
FIG. 1 is a perspective view of an embodiment of the implant according to the invention, attached to a rod of an osteosynthesis device.
Figure 2:
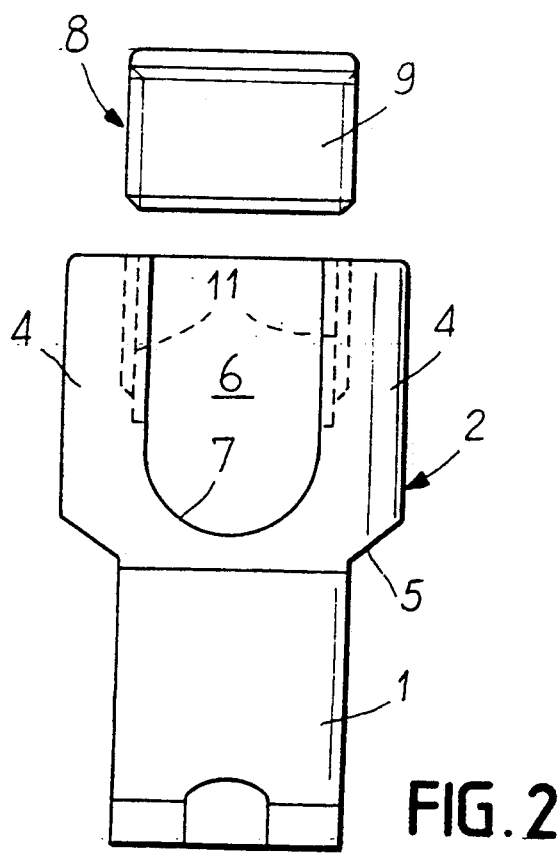
FIG. 2 is a front view of the implant in FIG. 1 in the axial direction of the rod, the plug being shown separate from the body.
Figure 3:
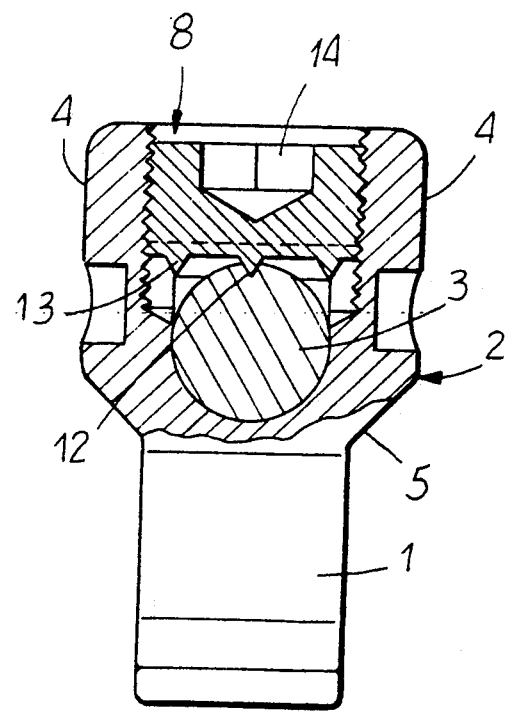
FIG. 3 is a transverse cutaway view of the implant in a plane perpendicular to the associated rod.
Figure 4:
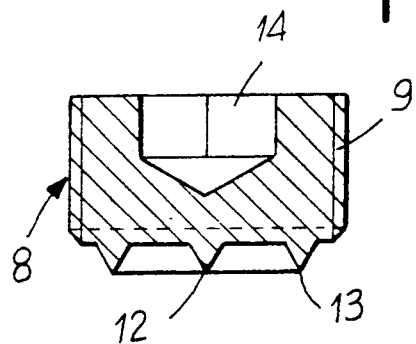
FIGS. 4 and 5 are an axial cutaway view and perspective view, respectively, of the plug of the implant.

The implant shown in FIGS. 1 to 6 is intended to form part of a device for osteosynthesis, in particular of the spine.

It comprises a portion intended for anchorage to bone, in this example consisting of a curved blade 1 which is known per se and which will not therefore be described, and a body 2 for attachment to a rod 3 whose surface is smooth or provided with rough features, such as diamond points.

The body 2 comprises, starting from the end of the blade 1, two side branches 4 connected to the blade 1 by a conical portion 5 and defining between them a channel 6, of which a rounded bottom 7 is contrived so as to be able to receive the rod 3, the channel 6 being open on the side opposite the rounded bottom 7. The channel 6 is open on both sides of the branches 4 in order to be able to receive the rod 3 between them.

The implant comprises a male plug 8 provided with a thread 9 and contrived so that it can be screwed into a female thread 11 formed in the inner walls of the two branches 4, closing the channel 6 on this side. The plug 8 is also contrived so that its two diametrically opposed edges bear on the rod 3, penetrating into the latter (FIG. 3) when completely screwed into the female thread 11.

According to an additional feature of the invention, that face 8a of the plug 8 directed towards the rod 3 is equipped with means of gripping and attaching the plug 8 to the latter, which can thus be clamped in translation and rotation.

In the embodiment described, these means of gripping comprise a central point 12 made integrally with the remainder of the plug 8, and a peripheral ring 13 projecting from the face 8a, triangular in section with an apex 13a preferably rounded, and made integrally with the remainder of the plug 8.

The rear portion of the plug 8, opposite the ring 13 and the point 12, has a profiled hole 14 for permitting its screwing into the female thread 11 by an appropriate instrument, this profile 14 being hexagonal for example. The female thread 11 of the two flanks or branches 4 of the body of the implant and the thread 9 of the plug 8 can be made with a saw-tooth pitch, in order to avoid the spreading of the two flanks 4 by completely eliminating the radial component of the load on screwing up.

Figure 6:
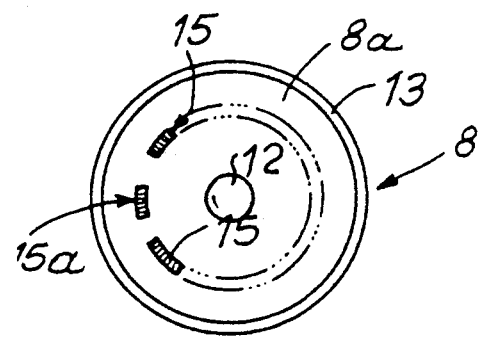
FIG. 6 is a plan view of that face of the plug directed towards the rod.
Figure 5:
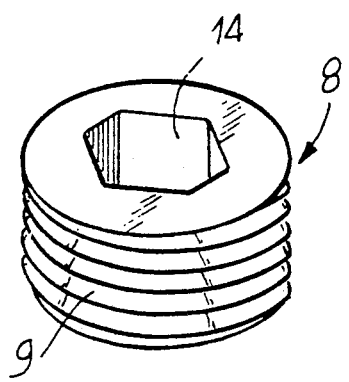

The plug 8 has, on its face 8a directed towards the rod 3, rough features 15 (FIG. 6). These rough features may advantageously be composed of a saw-tooth profile in which the oblique portions 15a are oriented in the direction of tightening of the plug 8. The latter is advantageously made by cold forming, for example cold hammering, which endows it with a hardness greater than that of the milled rod 3.

The anchoring blade 1, the body 2 and the plug 8 are made of the same biocompatible material, for example steel according to American Standard 316L, corresponding to the AFNOR Standard AS 1 Z2 CND 17.13.

The assembly of the implant, which has just been described, is very simple: the rod 3 is first introduced between the branches or flanks 4 into the channel 6, until it bears on the bottom 7. The plug 8 is then partially screwed into the female thread 11. The implant is loaded by detraction or compression or derotation, and the implant is then fixed by tightening the plug 8 by means of the tool corresponding to the profile of the hole 14. Finally, the final fixation is carried out by screwing the plug 8 until its central point 12 and its ring 13 penetrate into the rod 3, this penetration being made possible by the fact that the hardness of the material constituting the plug 8 is greater than that of the material of the rod 3. As a result of this, the ring 13 and the point 12 will prevent any loosening of the assembly, the point 12 and two diametrically opposed ends of the ring 13 in fact being sunk into the rod 3, as well as rough features 15.

At the end of these operations, the rod 3 is clamped both in rotation and in translation. The point 12 and the ring 13 ensure the safety of the fixation by acting as a nut retention.

Figure 7:
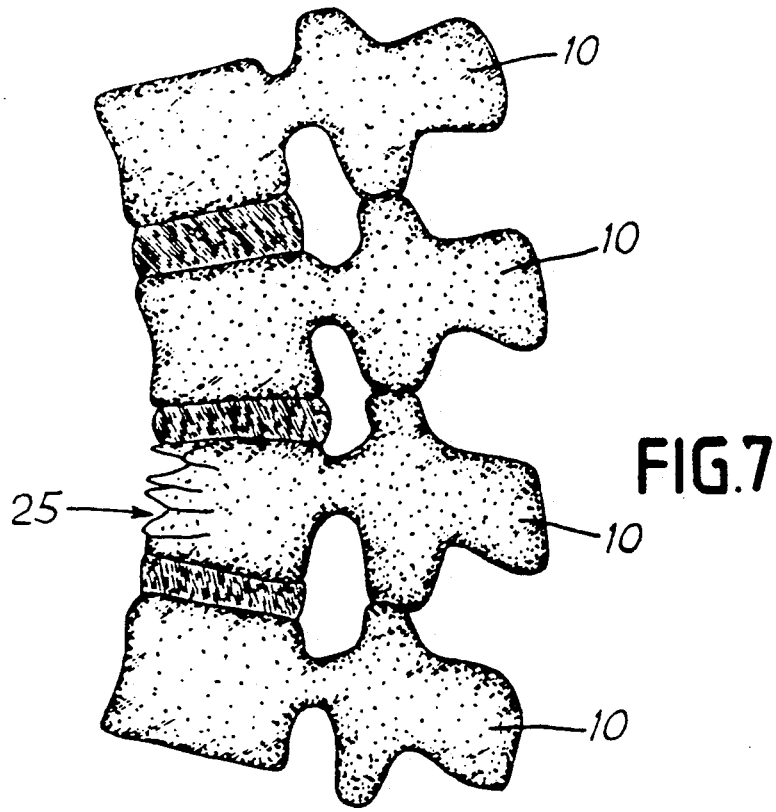
FIG. 7 is a view, in a sagittal plane, of vertebrae, one of which is fractured.
Figure 8:
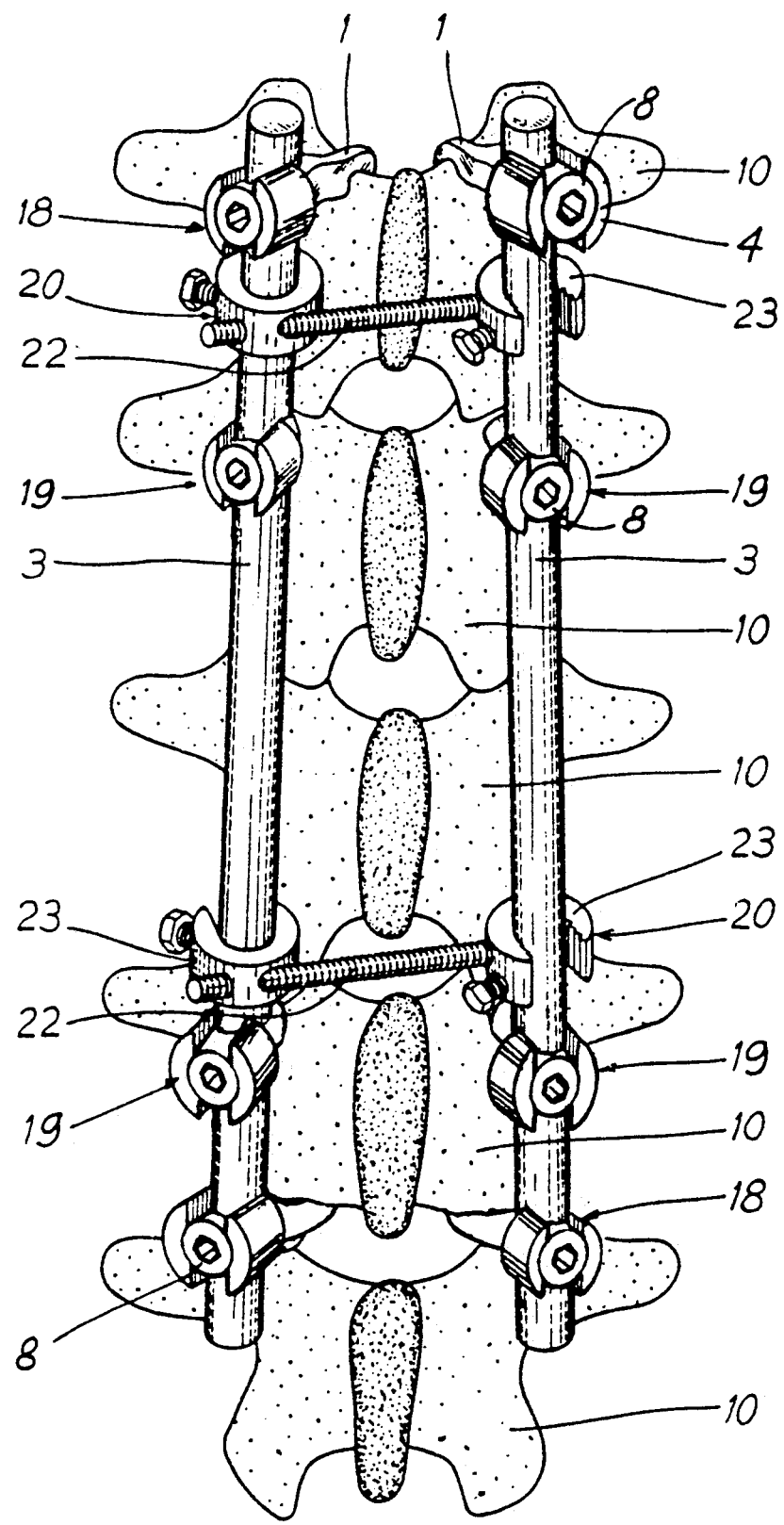
FIG. 8 is a view in a frontal plane of the fracture in FIG. 7, reduced by an osteosynthesis device provided with implants according to the invention.
Figure 9:
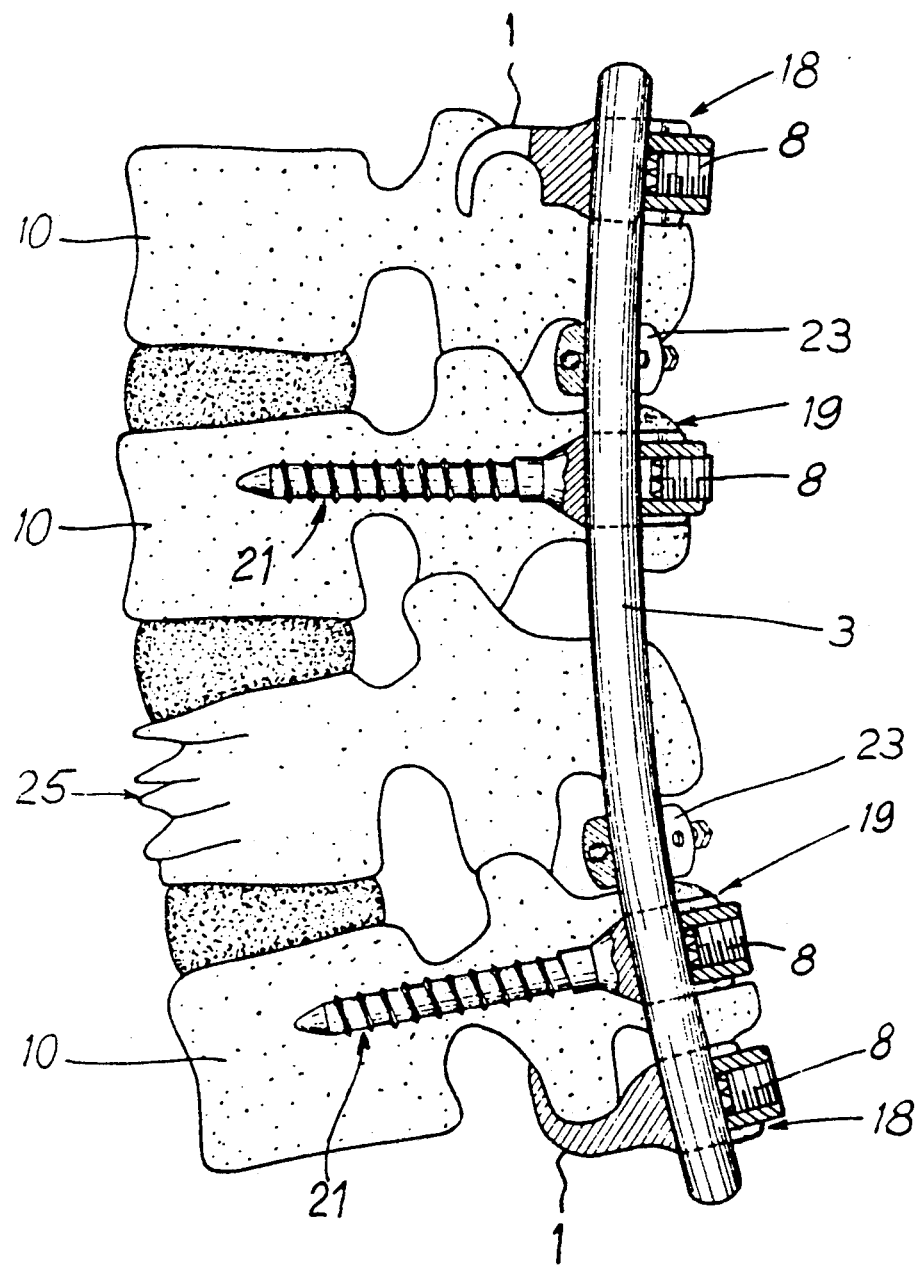
FIG. 9 is a view in the sagittal plane of the device in FIG. 8.

FIGS. 8 and 9 show the implantation of osteosynthesis instrumentation into vertebrae 10, one of which shows a fracture 25 (FIG. 7). This instrumentation comprises two devices 20 for stability and transverse traction (DTT) having transverse rods 22 and hooks 23 situated on the rods 3. The instrumentation is completed by several implants 18 and 19 similar to that described with reference to FIGS. 1-4, but with the difference, as regards the implants 19, that in the latter the portion for anchorage to bone does not consist of a curved blade 1, but of a threaded rod 21, the implants 18 and 19 being distributed as appropriate along the rods 3.

The implant according to the invention has the following advantages:

possibility of direct introduction of the rod 3 to the rear of the body 2 of the implant, without requiring complementary parts, such as intra-channel clamping devices;

possibility of effecting the compression and detraction (that is to say the extension of the spinal or osseous portion) without the need for a precise orientation of the head in the case of screw implants, whereas, on the other hand, a precise orientation is demanded by the conical form of the prior system;

considerable simplification of the instrumentation by reducing the different types of bodies used hitherto to a single type, open to the rear, and related simplification of the ancillary equipment;

considerable reduction in the external bulk of the implant by virtue of the plug 8 screwed into the internal female thread 11 of the flanks 4, the body 2 of the implant moreover being cylindrical;

elimination of all risks of deterioration of the female thread 11 of the flanks 4 by manipulation of the implant, by virtue of the fact that this female thread is arranged on the inside of the flanks 4;

reduction in the number of parts necessary, by virtue of the point 12 and the ring 13 made integrally with the plug 8, compared to an implant provided with a plug and a separate locking screw. The required instrumentation is thus reduced, and the assembly of the implant is simplified for the surgeon;

possibility of retensioning the device (when this becomes necessary as a result of the growth of a young subject) or simple ablation, the latter being necessary in particular in traumatology. Indeed, the implant can be disassembled very easily, first by unscrewing the plug 8;

finally, the ease of introducing the rod into the implant, in contrast to the difficulty at present of introducing this rod into a closed body.

As a variant, the plug 8 can be equipped with its central point 12 alone, or else with its ring 13 along.

What is claimed is:

1. Implant for an osteosynthesis device, in particular of the spine, comprising anchorage portion means for anchoring the implant to bone and body attaching means for attaching the implant to a rod, said body attaching means having two side branches defining a channel open at both sides of the body attaching means in order to be able to receive the rod and open to a rear portion of the body attaching means, and a threaded plug, a female thread formed in inner walls of said two side branches at the rear portion of the body attaching means, said threaded plug being screwed into said female thread to close the channel at said rear portion, the plug having a face directed towards the rod said face being equipped with means for gripping and attaching the plug to the rod in a manner in which the rod will be clamped to prevent translation and rotation.

2. Implant according to claim 1, wherein said means for gripping comprise a central point formed integrally with the plug.

3. Implant according to claim 1, wherein said means for gripping comprise a peripheral ring projecting from the face of the plug and formed integrally with the plug, said peripheral ring having a triangular cross-section and an apex, such that the apex of said peripheral ring will bear on the rod at two diametrically opposed points when the rod is clamped.

4. Implant according to claim 3, wherein the apex is rounded.

5. Implant according to claim 1, wherein said means for gripping comprise a central point and a peripheral ring projecting from the face of the plug, the central point and the peripheral ring being formed integrally with the plug.

6. Implant according to claim 1, wherein the anchorage portion means, the body attaching means and the plug are made of the same biocompatible material.

7. Implant according to claim 1, wherein the female thread formed in the inner walls of said two side branches of the body attaching means and the thread of the threaded plug are made with a saw-tooth pitch in order to prevent the plug from loosening when clamped against the rod.

8. Implant according to claim 1, wherein the face of the plug has rough features directed towards the rod.

9. Implant according to claim 8, wherein the rough features are composed of a saw-tooth profile in which an oblique portion is oriented in the direction of tightening.

10. Implant according to claim 1, wherein the plug is made by cold forming, which endows it with a hardness greater than that of a milled rod.

11. Implant according to claim 9, wherein the method of the cold forming is by cold hammering.

* * * * *